(12) United States Patent
Algawi et al.

(10) Patent No.: US 11,737,821 B2
(45) Date of Patent: Aug. 29, 2023

(54) BUBBLE DETECTOR ON PROXIMAL END OF CATHETER WITH FAIL-SAFE MECHANISM

(71) Applicant: Biosense Webster (Israel) Ltd., Yokneam (IL)

(72) Inventors: Yehuda Algawi, Binyamina (IL); Assaf Govari, Haifa (IL); Andres Claudio Altmann, Haifa (IL); Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 1005 days.

(21) Appl. No.: 16/526,764

(22) Filed: Jul. 30, 2019

(65) Prior Publication Data

US 2021/0030465 A1 Feb. 4, 2021

(51) Int. Cl.
*A61B 18/14* (2006.01)
*A61B 17/00* (2006.01)
(Continued)

(52) U.S. Cl.
CPC .... *A61B 18/1492* (2013.01); *A61B 17/00234* (2013.01); *A61M 1/77* (2021.05);
(Continued)

(58) Field of Classification Search
CPC ........ A61B 17/00234; A61B 2017/003; A61B 18/1492; A61B 2018/00011; A61B 2018/00577; A61B 2018/00744; A61B 2217/005; A61B 2217/007; A61B 2218/002; A61B 2090/065;
(Continued)

(56) References Cited

U.S. PATENT DOCUMENTS 5,053,747 A 10/1991 Slate et al.
2008/0098798 A1 5/2008 Riley et al.
(Continued)

FOREIGN PATENT DOCUMENTS

CN 208 611 483 U 3/2019
CN 109789269 A 5/2019
(Continued)

OTHER PUBLICATIONS

Extended European Search Report issued in European Patent Application No. 20 18 8421 dated Dec. 3, 2020.

*Primary Examiner* — Khadijeh A Vahdat
(74) *Attorney, Agent, or Firm* — Troutman Pepper Hamilton Sanders LLP

(57) ABSTRACT

A system includes a probe, a processor, and a bubble detector. The probe is configured for insertion into a lumen of a patient and is coupled to an irrigation pump. The processor is configured to control delivery of irrigation fluid to the probe by turning on and controlling the irrigation pump. The bubble detector is coupled to a proximal portion of the probe. In response to the irrigation pump being turned on, the bubble detector is configured to automatically start detection of gas bubbles in the irrigated fluid, and transmit fail-safe signals indicating fail-safe bubble detection is operational. The processor is further configured to monitor the fail-safe signals and, in absence of fail-safe signals, to automatically disable delivery of the irrigation fluid.

14 Claims, 2 Drawing Sheets

(51) Int. Cl.
*A61M 5/36* (2006.01)
*A61M 1/00* (2006.01)
*A61M 3/02* (2006.01)
*A61B 18/00* (2006.01)

(52) U.S. Cl.
CPC .......... *A61M 3/0258* (2013.01); *A61M 5/365* (2013.01); *A61B 2017/003* (2013.01); *A61B 2018/00011* (2013.01); *A61B 2018/00577* (2013.01); *A61B 2018/00744* (2013.01); *A61B 2217/005* (2013.01); *A61B 2217/007* (2013.01); *A61B 2218/002* (2013.01); *A61M 2209/02* (2013.01); *G01N 2291/02433* (2013.01)

(58) Field of Classification Search
CPC .......... A61M 2205/17; A61M 2205/18; A61M 2209/02; A61M 3/0258; A61M 5/365
See application file for complete search history.

(56) References Cited

U.S. PATENT DOCUMENTS

| | | | |
|---|---|---|---|
| 2011/0071511 A1* | 3/2011 | Brannan | A61B 18/1233 606/33 |
| 2014/0243821 A1 | 8/2014 | Salahieh et al. | |
| 2019/0054256 A1 | 2/2019 | Peri et al. | |
| 2019/0054276 A1 | 2/2019 | Werneth et al. | |

FOREIGN PATENT DOCUMENTS

| | | | |
|---|---|---|---|
| EP | 0053453 A1 | 6/1982 | |
| EP | 3076137 B1 | 1/2019 | |

* cited by examiner

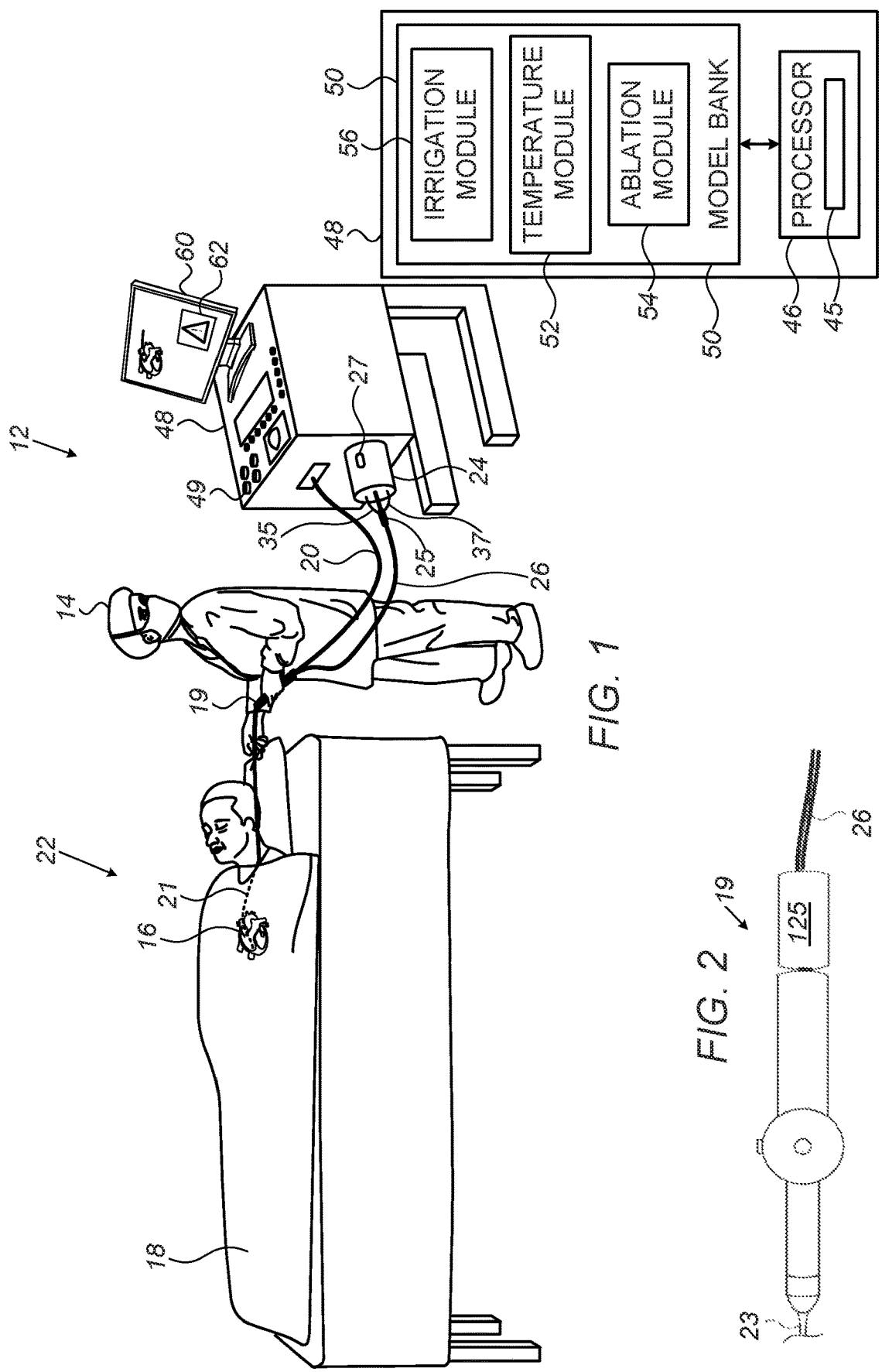

US 11,737,821 B2

BUBBLE DETECTOR ON PROXIMAL END OF CATHETER WITH FAIL-SAFE MECHANISM

FIELD OF THE INVENTION

The present invention relates generally to invasive procedures, and specifically to monitoring of irrigation fluid used during invasive procedures.

BACKGROUND OF THE INVENTION

During some invasive medical procedures, tissue may be irrigated, and the irrigation fluid used may be monitored for the occurrence of bubbles. A number of bubble monitoring techniques were previously proposed in the patent literature. For example, EP0053453, EP3076137, CN109789269 each describes a bubble detection system. U.S. Patent Application Publication 2019/054256 describes a method, including ejecting irrigation fluid from a distal end of a probe so as to irrigate tissue, and receiving, over a period of time, initial signals indicative of respective temperatures of the distal end, from a temperature sensor in the distal end. The method also includes formulating from the initial signals a temperature range between upper and lower temperature thresholds and, when a further signal from the temperature sensor, received subsequent to the period of time, is indicative of a further temperature above the upper temperature threshold, raising an alarm that a bubble is present in the irrigation fluid. All of the documents referenced are hereby incorporated by reference as if set forth herein with a copy in the Appendix.

SUMMARY OF THE INVENTION

An embodiment of the present invention provides a medical system including a probe, a processor, and a bubble detector. The probe is configured for insertion into a lumen of a patient and is coupled to an irrigation pump. The processor is configured to control delivery of irrigation fluid to the probe by turning on and controlling the irrigation pump. The bubble detector is coupled to a proximal portion of the probe. In response to the irrigation pump being turned on, the bubble detector is configured to automatically start detection of gas bubbles in the irrigated fluid, and transmit fail-safe signals indicating fail-safe bubble detection is operational. The processor is further configured to monitor the fail-safe signals and, in absence of fail-safe signals, to automatically disable delivery of the irrigation fluid.

In some embodiments, the processor is further configured to alert a user that the delivery of the irrigation fluid is disabled.

In some embodiments, the bubble detector is configured to transmit the fail-safe signals every prespecified time interval.

In an embodiment, the processor is further configured to present to a user an option to override, for a given time duration, the automatic disabling of the delivery of the irrigation fluid.

In another embodiment, the bubble detector is electrically wired to power leads of the irrigation pump, and is thus configured to start the detection in response to the irrigation pump being turned on.

In some embodiments, the bubble detector is wired in parallel to an auxiliary power source that retains the bubble detector in a ready mode, so as to start operating within a given time delay after the irrigation pump is turned on.

In some embodiments, the bubble detector is wired in parallel to an auxiliary power source that powers the bubble detector regardless of whether the irrigation pump is turned on or off.

In an embodiment, the system further includes a drip detector, which is attached to a drip chamber of a saline bag that contains saline for use during purge. The drip detector is configured to send to the irrigation pump an indication that saline is dripping out of the bag, and if no indication is sent, a pump logic is configured to disable a purge button.

In another embodiment, the pump logic is further configured, if no indication is sent from the drip detector, and an indication of decreasing level of saline in the drip chamber is received from a level indicator attached to a drip chamber, to terminate any ablation currently occurring and reduce the flow rate to an idle flow.

There is additionally provided, in accordance with an embodiment of the present invention, a method including inserting a probe into a lumen of a patient, wherein the probe is coupled to an irrigation pump. Delivery of irrigation fluid to the probe is controlled by turning on and controlling the irrigation pump. In response to the irrigation pump being turned on, a bubble detector coupled to a proximal portion of the probe is controlled to automatically start detection of gas bubbles in the irrigated fluid, and to transmit fail-safe signals indicating fail-safe bubble detection is operational. The fail-safe signals are monitored and, in absence of fail-safe signals, delivery of the irrigation fluid is automatically disabled.

The present disclosure will be more fully understood from the following detailed description of the embodiments thereof, taken together with the drawings, in which:

BRIEF DESCRIPTION OF THE DRAWINGS

FIG. 1 is a schematic illustration of a catheter-based cardiac ablation system, according to an embodiment of the present invention;

FIG. 2 is a schematic, pictorial illustration of a bubble detector coupled to a proximal end of a catheter handle, according to an embodiment of the present invention;

DETAILED DESCRIPTION OF EMBODIMENTS

Overview

Figure 3:
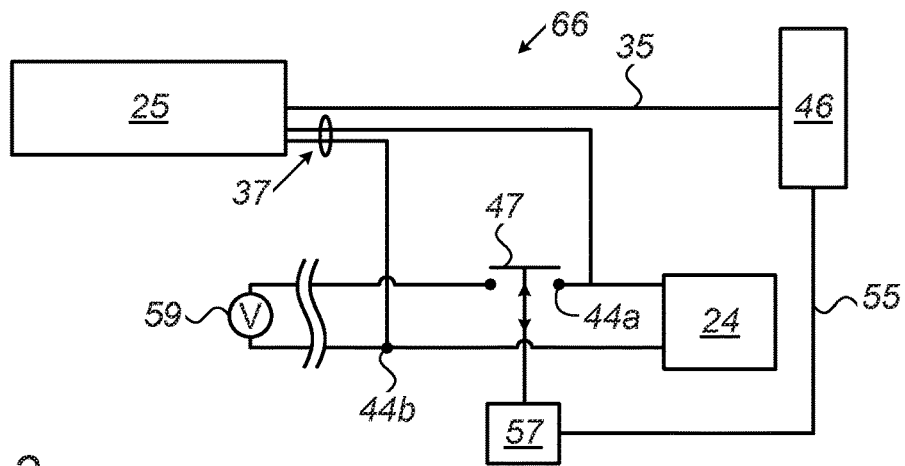
FIG. 3 is a block diagram that schematically describes a fail-safe architecture used during the ablation procedure described by FIG. 1, according to an embodiment of the present invention.

There are a number of invasive procedures, such as an ablation procedure of an internal organ, where tissue undergoing the procedure is irrigated. In some cases, bubbles may be created in the irrigation fluid, which, if reaching the patient undergoing the procedure, may cause safety issues. Mechanisms for detecting bubbles at an irrigation pump used to pump the irrigation fluid may, as described below, fail to operate to detect the bubbles.

Embodiments of the present invention that are described hereinafter provide fail-safe bubble detection systems comprising a bubble detector located at a proximal portion of a probe, such as a catheter, for insertion into a lumen of a patient. In the disclosed embodiment, "a proximal portion"

means a portion of the probe which is outside the body of the patient. The probe is connected to a console that includes a processor-controlled irrigation pump for delivering irrigation fluid via the probe to irrigate tissue. The bubble detector has a fail-safe mechanism to ensure that the detector starts to detect possible gas bubbles in the streamed fluid in response to the irrigation pump being turned on.

In some embodiments, a fail-safe wiring architecture is provided, in which the bubble detector is connected to the irrigation pump in a way such that, whenever the irrigation pump starts operating, the bubble detector automatically starts its operation as well. For example, the bubble detector may be wired to power leads located on the irrigation pump.

In some embodiments, the bubble detector periodically transmits fail-safe signals while operating that indicate proper operation of the bubble detection system. The processor receives these fail-safe signals, and, in the absence of the fail-safe signals, is configured to turn off the irrigation pump and alert a user that irrigation is disabled. Alternatively, the processor first alerts the user, and only subsequently, within a prespecified duration, turns off the irrigation pump.

In some embodiments, the processor is further configured to present to the user an option to override the automatic disabling of irrigation for a given time duration and allow the irrigation pump to continue operation before being automatically turned off. In an embodiment, the given duration may be further extended by the user.

In some embodiments, a disclosed system for bubble detection is provided as an add-on to legacy systems, to overcome potentially hazardous medical scenarios in which irrigation is not sufficiently monitored for bubbles despite the system being equipped with a gas bubble detection sub-system.

By locating an additional bubble detector with fail-safe mechanisms at a proximal portion of a probe, embodiments of the present invention may enhance patient safety during an invasive medical procedure that requires irrigation.

Bubble Detector on Proximal End of Catheter with Fail-Safe Mechanism

FIG. 1 is a schematic illustration of a catheter-based cardiac ablation system 12, according to an embodiment of the present invention. System 12 is used by a physician 14 to perform an invasive procedure, which, by way of example, is assumed to comprise radiofrequency (RF) ablation of a portion of a myocardium 16 of the heart of a patient 18.

In order to perform the ablation, physician 14 uses a catheter handle 19 to insert a catheter 20 into a sheath 21 that has been pre-positioned in a lumen of the patient. Sheath 21 is positioned so that a distal end 22 of the catheter may enter the heart of the patient, after exiting a distal end of the sheath, and then contact tissue of the heart.

System 12 is controlled by a system processor 46 and interface circuitry 45. The processor can be programmed to perform at least one algorithm disclosed herein, the algorithm comprising steps described hereinbelow. The processor uses interface circuitry 45 in order to perform the algorithm.

Processor 46 is located in an operating console 48 of system 12. Console 48 comprises controls 49 which are used by physician 14 to communicate with processor 46, which communicates with modules in a module bank 50 to implement the procedure. The functions of modules in bank 50 are described below.

During the procedure performed by physician 14, distal end 22 is supplied with irrigation fluid, typically heparinized normal saline solution, pumped by an irrigation pump 24. In some embodiments irrigation pump 24 comprises a peristaltic pump; alternatively, any other suitable irrigation fluid pump may be used.

An irrigation module 56 of processor 46 controls the rate of flow of the fluid from pump 24 to catheter 20 via irrigation tubing 26. Irrigation module 56, under overall control of processor 46, is typically configured to vary, as needed, the rate of fluid flow from a zero rate up to a predefined maximum rate. In one embodiment, once distal end 22 has been inserted into sheath 21, module 56 operates pump 24 to provide a minimal fluid flow rate of approximately 5 ml/min, which is increased by the module when physician 14 begins ablation.

Irrigation pump 24 further comprises a bubble detection sub-system 27, which operates while irrigation fluid is being provided to the catheter. Bubble detection sub-system 27 is disposed proximate an outlet of irrigation pump 24. If a bubble is detected by sub-system 27, the flow of irrigation fluid is typically halted automatically by processor 46. In some cases, however, processor 46 initially raises an alarm to physician 14 regarding the presence of bubbles in the irrigation fluid. The alarm may be an auditory non-verbal warning, such as a ring, or a recorded statement that is broadcast to the physician. Alternatively or additionally, the alarm may be a visual warning, such as a light that is switched on, or a warning notice 62 on screen 60.

Bubble detection sub-system 27 is normally disabled automatically during a "purge" phase (also termed a "splash") that is used to clear the irrigation tubes. The purge phase is usually not invoked while catheter 20 is inserted into a patient, however, such an event may occur accidentally. In this case, bubble detection sub-system 27 may have no way of detecting if a bubble enters the patient, with consequent problems.

Embodiments of the present invention provide an extra bubble detector 25 to protect against events of irrigation operating with bubbles that are not prevented by detection sub-system 27. Bubble detector 25 is connected to irrigation pump 24 via a cable 37, in a fail-safe scheme ensuring that whenever irrigation pump 24 is turned on, bubble detector 25 automatically starts operation to detect bubbles. However, in order to enable purge, in one embodiment, bubble detector 25 turns off when the physician pushes a dedicated purge button for initiating a purge. In another embodiment, bubble detector 25 is disconnected from the proximal portion of the catheter whenever a purge (e.g., a splash) is done, and only afterwards the physician connects bubble detector 25 to the catheter.

For example, a fail-safe scheme may be realized by bubble detector 25 being wired directly to the power leads of irrigation pump 24. In some embodiments, bubble detector 25 may be connected to irrigation pump 24 via a cable. In other embodiments, a logic is used for the fail-safe scheme, with bubble detector 25 connected wirelessly to a control of irrigation pump 24, to trigger the disabling of pump 24.

In an optional embodiment, a drip detector or a level indicator is attached to a drip chamber of a saline bag that contains saline for use during purge. The drip detector sends to the irrigation pump an indication that saline is flowing out of the bag. If no indication is sent (as there is no saline flowing out of the bag) then a pump logic is configured to disable a purge button, described below, as the bag is empty.

In an optional embodiment, the pump logic may be configured to identify when there are no drops, but the level indicator is decreasing (indicating that the saline is flowing but the bag is empty). In this scenario, the pump logic can terminate any ablation currently occurring and reduce the flow rate to idle flow. This can allow the physician sufficient time to replace the empty IV bag before air is drawn into the tubing and the irrigation is forced to stop. The combination of both a drop counter and a level indicator can also allow for identification of occlusion, whether from a closed stopcock or an occluded device.

Bubble detector 25 is located (e.g., incorporated into or fitted over) a proximal portion of catheter 20 and is configured to transmit signals to processor 46 via a cable 35 in response to bubbles detected in the irrigation fluid. The processor is configured to halt the irrigation flow if the extra bubble detector detects a bubble. Thus, even if bubble detection sub-system 27 of irrigation pump 24 is disabled, irrigation can be disabled when bubbles are detected.

Figure 4:
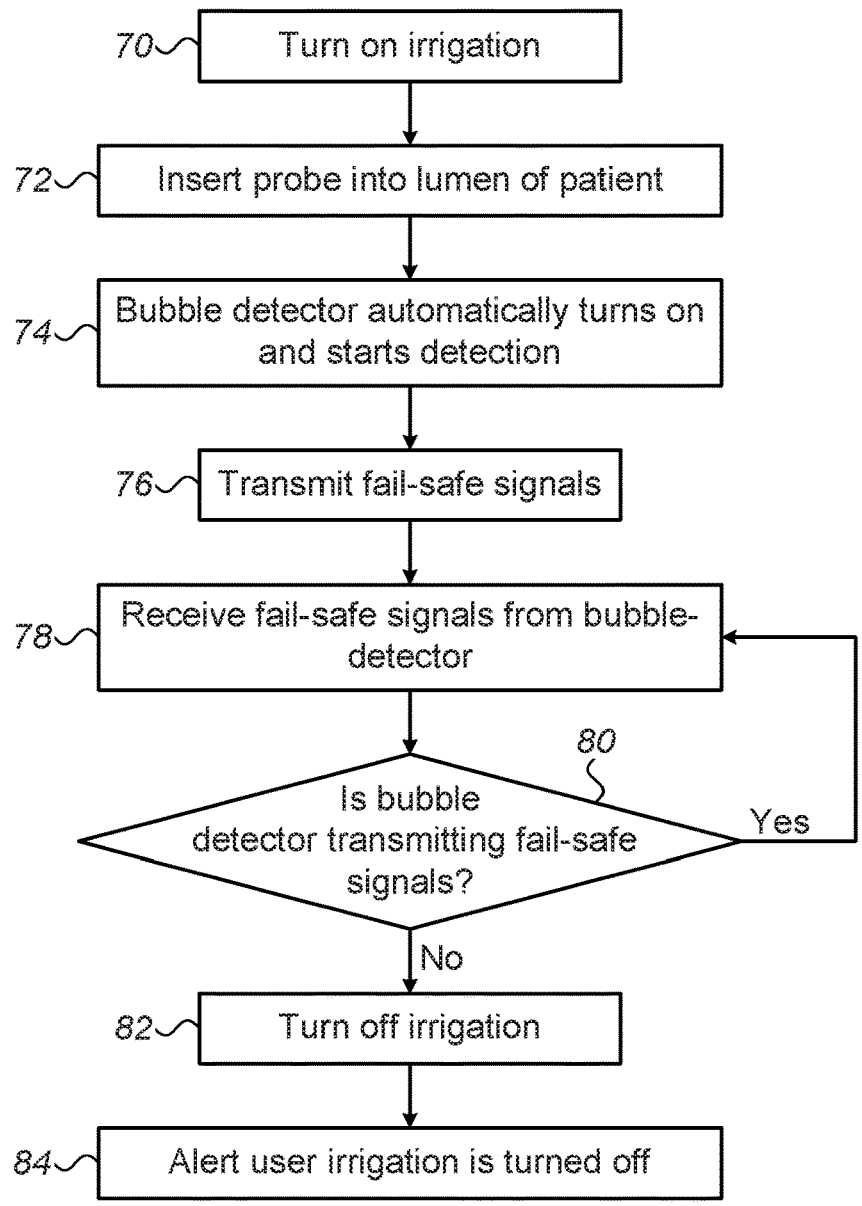
FIG. 4 is a flow chart of steps of an algorithm performed during the procedure described in FIG. 1 and with the fail-safe architecture described in FIG. 3, according to an embodiment of the present invention.

In some embodiments, bubble detector 25 is an add-on to legacy probes, for example by fitting the detector on an irrigation tube of catheter 20 and electrically connecting bubble detector 25 to console 48 to perform the steps described in FIG. 4. At the same time, processor 46, or another controller of irrigation pump 24, is configured to perform steps responsively to signals from bubble detector 25, as also described below in FIG. 4.

In some embodiments, bubble detector 25 functions in a fail-safe mode to ensure that irrigation is disabled unless bubble sensor 25 actively indicates that it is operating. In an embodiment, bubble detector 25 is configured to transmit a fail-safe signal to processor 46 via a cable 35 to indicate that bubble detector 25 is active at a prespecified time interval (e.g., periodically). Processor 46 in configured to turn off irrigation pump 24 unless such a fail-safe signal is received within a prespecified duration. The prespecified duration and time-interval are adjustable. In another embodiment, the processor alerts physician 14, using one of the methods described above, before disabling irrigation.

In another embodiment, bubble detector 25 includes a self-test, such as exist in the industry, to detect failure of detector 25, whereby bubble detector 25 is configured to stop sending the fail-safe signals via cable 35 in case such failure is self-detected.

Processor 46 uses a temperature module 52 to analyze signals received from temperature sensors in distal end 22. From the analyzed signals, processor 46 determines temperatures of the distal end, and, in an embodiment, uses the sensed temperatures in a bubble-detection algorithm described in the aforementioned U.S. Patent Application Publication 2019/054256 filed Aug. 15, 2017, entitled "Detection of Bubbles in Irrigation Fluid," which is assigned to the assignee of the present patent application and whose disclosure is incorporated herein by reference.

Module bank 50 also comprises an ablation module 54, which enables processor 46 to inject RF current via selected electrodes of distal end 22 (described below), and returning electrodes on the skin of the patient (not shown in the diagram), into myocardium 16, in order to ablate regions of the myocardium which are in contact with the selected electrodes. The ablation module also enables the processor to set parameters of the injected current, such as its frequency, the power dissipated, and the duration of the injection.

In order to operate system 12, module bank 50 typically comprises modules other than those described above, such as a force module enabling the processor to measure a force on the distal end, and an electrocardiogram (ECG) module enabling the processor to acquire electro-potentials from myocardium 16 via electrodes in the distal end. For simplicity, other such modules are not illustrated in FIG. 1. All modules may comprise hardware as well as software elements.

The software for processor 46 and the modules of module bank 50 may be downloaded to the processor in electronic form, over a network, for example. Alternatively or additionally, the software may be provided on non-transitory tangible media, such as optical, magnetic, or electronic storage media. The processor, and typically the modules, comprise memory used to store the downloaded software, as well as to store data generated by system 12.

Processor 46 may present results of the procedure performed by physician 14, as well as results of the algorithm described below with reference to FIG. 4, on a display screen 60.

Fail-Safe Bubble Detection

FIG. 2 is a schematic, pictorial illustration of a bubble detector 125 coupled to a proximal end of a catheter handle 19, according to an embodiment of the present invention. In this embodiment, physician 14 can readily disconnect bubble detector 125 from the proximal portion of the catheter whenever a purge (e.g., a splash) is done, and only afterwards physician 14 reconnects bubble detector 125 to handle 19 to provide the disclosed fail-safe configuration.

FIG. 3 is a block diagram that schematically describes a fail-safe architecture 66 used during the ablation procedure described by FIG. 1, according to an embodiment of the present invention. As seen, pump 24 is connected to an electromotive power source 59. Processor 46 can instruct, via a line 55, a relay device 57 to close or open a switch 47, and thereby switch pump 24 on and off, respectively. In FIG. 3, bubble detector 25 is wired parallel to pump 24 in a fail-safe power wiring scheme, where the detector is wired to power leads 44a and 44b of the irrigation pump. This fail-safe power wiring scheme ensures that bubble detector 25 is switched on whenever pump 24 receives operating power.

While operating, bubble detector 25 sends fail-safe signals to processor 46 via line 35, for processor 46 to regularly verify that bubble detector 25 is properly operating. If processor 46 stops receiving the fail-safe signals, processor 46 directs relay 57, via a command line 55, to open switch 47 so as to turn off irrigation pump 24 and stop the flow of irrigation fluid. Examples of fail-safe signals are signals that give an effective temperature in the vicinity of bubble-detector 25 via a temperature sensor that works only if bubble detector 25 is active.

In an optional embodiment, bubble detector 25 is wired in parallel to another power source (not shown) that enables the bubble detector to be in a ready mode, so as to start operating within a given time delay after the irrigation pump is turned on. In another optional embodiment, the other power source enables the bubble detector to operate regardless whether the irrigation pump is turned on or turned off.

The example of the fail-safe architecture 66 shown in FIG. 3 was chosen purely for the sake of conceptual clarity. In practice, a fail-safe mechanism may be devised differently, or include additional elements (e.g., an uninterruptible power supply (UPS)), as would occur to a person having ordinary skills in the art.

FIG. 4 is a flow chart of steps of an algorithm performed during the procedure described in FIG. 1 and with the fail-safe architecture 66 described in FIG. 3, according to an embodiment of the present invention.

The algorithm, according to the presented embodiment, carries out a process that begins with physician 14 first activating irrigation, including turning on pump 24, purging the irrigation channel and establish idle flow rate, in a turning on irrigation step 70. Next, physician 14 inserts catheter 20, which is plugged into console 48 and coupled to irrigation pump 24, into a sheath 21 that has been pre-positioned in a lumen of patient 18, at a catheter insertion step 72.

By being wired to irrigation pump 24 according to fail-safe architecture 66 and, bubble detector 25, which is located at a proximal portion of catheter 20, is automatically turned on and commences bubble detection, at a bubble detection step 74. However, in order to enable step 70, in one embodiment, bubble detector 25 turns off when the physician pushes a dedicated button for initiating a purge.

Bubble detector 25 transmits fail-safe signals to indicate that the detector is properly carrying out bubble detection, at a fail-safe signaling step 76.

The fail-safe signals are received, at a receiving fail-safe signals step 78, by processor 46 that controls irrigation module 24.

Processor 46 continuously checks that the fail-safe signals are received, as required, during every prespecified time interval, in a fail-safe checking step 80. As long as the fail-safe signals are received the process returns to step 78 to continue monitoring. If processor 46 does not receive fail-safe signals within the prespecified duration, processor 46 then instructs turning off irrigation pump 24, at a fail-safe turning off step 82. At the same time, processor 46 issues an alert to the user, e.g., by the audiovisual methods described above, that irrigation is being turned off, at an alerting step 84.

Although the embodiments described herein mainly address cardiac applications, the methods and systems described herein can also be used in other clinical applications, such as in any invasive medical procedures that require flowing liquid into a body of a patient during procedure.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A system for a medical catheter, comprising:
   a probe for insertion into a lumen of a patient, wherein the probe is coupled to an irrigation pump;
   a bubble detection sub-system disposed proximate an outlet of the irrigation pump;
   a processor, which is configured to control delivery of irrigation fluid to the probe by turning on and controlling the irrigation pump;
   a bubble detector coupled to a proximal portion of the probe, wherein, in response to the irrigation pump being turned on, the bubble detector is configured to:
      automatically start detection of gas bubbles in the irrigated fluid; and
      transmit fail-safe signals every prespecified time interval indicating fail-safe bubble detection is operational; and
   wherein the processor is further configured to monitor the fail-safe signals and, in absence of fail-safe signals, to automatically disable delivery of the irrigation fluid.

2. The system according to claim 1, wherein the processor is further configured to alert a user that the delivery of the irrigation fluid is disabled.

3. The system according to claim 1, wherein the bubble detector is electrically wired to power leads of the irrigation pump, and is thus configured to start the detection in response to the irrigation pump being turned on.

4. The system according to claim 1, wherein the bubble detector is wired in parallel to an auxiliary power source that retains the bubble detector in a ready mode, so as to start operating within a given time delay after the irrigation pump is turned on.

5. The system according to claim 1, wherein the bubble detector is wired in parallel to an auxiliary power source that powers the bubble detector regardless of whether the irrigation pump is turned on or off.

6. A system for a medical catheter, comprising:
   a probe for insertion into a lumen of a patient, wherein the probe is coupled to an irrigation pump;
   a bubble detection sub-system disposed proximate an outlet of the irrigation pump;
   a processor, which is configured to control delivery of irrigation fluid to the probe by turning on and controlling the irrigation pump;
   a bubble detector coupled to a proximal portion of the probe, wherein, in response to the irrigation pump being turned on, the bubble detector is configured to:
      automatically start detection of gas bubbles in the irrigated fluid; and
      transmit fail-safe signals indicating fail-safe bubble detection is operational; and
   wherein the processor is further configured to monitor the fail-safe signals and, in absence of fail-safe signals, to automatically disable delivery of the irrigation fluid, wherein the processor is further configured to present to a user an option to override, for a given time duration, the automatic disabling of the delivery of the irrigation fluid.

7. The system according to claim 6, wherein the bubble detector is electrically wired to power leads of the irrigation pump, and is thus configured to start the detection in response to the irrigation pump being turned on.

8. The system according to claim 6, wherein the bubble detector is wired in parallel to an auxiliary power source that retains the bubble detector in a ready mode, so as to start operating within a given time delay after the irrigation pump is turned on.

9. The system according to claim 6, wherein the bubble detector is wired in parallel to an auxiliary power source that powers the bubble detector regardless of whether the irrigation pump is turned on or off.

10. A system for a medical catheter, comprising:
    a probe configured to be inserted into a lumen of a patient, and coupled to an irrigation pump;
    a bubble detection sub-system disposed proximate an outlet of the irrigation pump;
    a processor, configured to control delivery of irrigation fluid to the probe by turning on and controlling the irrigation pump;
    a bubble detector coupled to a proximal portion of the probe, wherein, in response to the irrigation pump being turned on, the bubble detector is configured to:
       automatically start detection of gas bubbles in the irrigated fluid; and transmit fail-safe signals indicating fail-safe bubble detection is operational;

a drip detector, which is attached to a drip chamber of a saline bag that contains saline for use during purge, wherein the drip detector is configured to send to the irrigation pump an indication that saline is dripping out of the bag, and wherein if no indication is sent, a pump logic is configured to disable a purge button, and wherein the processor is further configured to monitor the fail-safe signals and, in absence of fail-safe signals, to automatically disable delivery of the irrigation fluid.

11. The system according to claim 10, wherein the pump logic is further configured, if no indication is sent from the drip detector, and an indication of decreasing level of saline in the drip chamber is received from a level indicator attached to a drip chamber, to terminate any ablation currently occurring and reduce the flow rate to an idle flow.

12. The system according to claim 10, wherein the bubble detector is electrically wired to power leads of the irrigation pump, and is thus configured to start the detection in response to the irrigation pump being turned on.

13. The system according to claim 10, wherein the bubble detector is wired in parallel to an auxiliary power source that retains the bubble detector in a ready mode, so as to start operating within a given time delay after the irrigation pump is turned on.

14. The system according to claim 10, wherein the bubble detector is wired in parallel to an auxiliary power source that powers the bubble detector regardless of whether the irrigation pump is turned on or off.

* * * * *